United States Patent [19]

Thome

[11] Patent Number: 5,645,528
[45] Date of Patent: Jul. 8, 1997

[54] UNITARY TIP AND BALLOON FOR TRANSURETHRAL CATHETER

[75] Inventor: Scott P. Thome, Waite Park, Minn.

[73] Assignee: Urologix, Inc., Minneapolis, Minn.

[21] Appl. No.: 468,801

[22] Filed: Jun. 6, 1995

[51] Int. Cl.⁶ .................................................. A61M 29/00
[52] U.S. Cl. ................................ 604/96; 604/113; 604/194
[58] Field of Search .............................. 604/96, 113, 114, 604/102, 97–100, 103, 264, 280–284; 606/108, 192, 32, 33, 27, 194; 128/656, 657, 658, 772, 673

[56] References Cited

U.S. PATENT DOCUMENTS

| | | | |
|---|---|---|---|
| 550,238 | 11/1895 | Allen, Jr. | |
| 2,642,874 | 6/1953 | Keeling | 128/349 |
| 2,813,531 | 9/1957 | Lee | 128/350 |
| 2,936,761 | 5/1960 | Snyder | 128/349 |
| 3,125,096 | 3/1964 | Antiles et al. | 128/401 |
| 3,977,408 | 8/1976 | MacKew | 128/349 B |
| 4,224,929 | 9/1980 | Furihata | 128/5 |
| 4,423,725 | 1/1984 | Baran et al. | 128/207.15 |
| 4,445,892 | 5/1984 | Hussein et al. | 604/101 |
| 4,497,324 | 2/1985 | Sullivan et al. | 128/736 |
| 4,559,951 | 12/1985 | Dahl et al. | 128/642 |
| 4,610,662 | 9/1986 | Weikl et al. | 604/53 |
| 4,662,383 | 5/1987 | Sogawa et al. | 128/784 |
| 4,676,258 | 6/1987 | Inokuchi et al. | 128/804 |
| 4,763,654 | 8/1988 | Jang | 128/344 |
| 4,777,951 | 10/1988 | Cribier et al. | 128/344 |
| 4,813,429 | 3/1989 | Eshel et al. | 128/736 |
| 4,832,023 | 5/1989 | Murphy-Chutorian et al. | 128/303.1 |
| 4,850,969 | 7/1989 | Jackson | 604/96 |
| 4,911,163 | 3/1990 | Fina | 606/127 |
| 4,921,483 | 5/1990 | Wijay et al. | 604/96 |
| 4,924,863 | 5/1990 | Sterzer | 606/27 |
| 4,932,958 | 6/1990 | Reddy et al. | 606/192 |
| 4,946,449 | 8/1990 | Davis, Jr. | 604/256 |
| 4,955,377 | 9/1990 | Lennox et al. | 128/401 |
| 4,961,738 | 10/1990 | Mackin | 606/15 |
| 4,967,765 | 11/1990 | Turner et al. | 128/785 |
| 5,190,540 | 3/1993 | Lee | 606/28 |
| 5,257,977 | 11/1993 | Eshel | 604/113 |
| 5,395,331 | 3/1995 | O'Neill et al. | 604/96 |

FOREIGN PATENT DOCUMENTS

| | | |
|---|---|---|
| 0341988A1 | 5/1988 | European Pat. Off. . |
| 0370890A1 | 11/1988 | European Pat. Off. . |
| 3534124A1 | 4/1987 | Germany . |

OTHER PUBLICATIONS

*Heating characteristics of a helical microwave applicator for transurethral hyperthermia of benign prostatic hyperplasia*, M. Astrahan et al., Int. J. Hyperthermia, 1991, vol. 7, No. 1, 141–155.

Primary Examiner—Corrine M. McDermott
Assistant Examiner—Cris L. Rodriguez
Attorney, Agent, or Firm—Kinney & Lange, P.A.

[57] ABSTRACT

An intraurethral catheter includes an elongate shaft and a tip comprising a unitary member including a curved tip portion and an inflatable balloon portion mountable on a proximal end of the catheter shaft. The present invention simplifies manufacture of the catheter by permitting an inflatable retention balloon and a curved insertion tip to be simultaneously secured on a proximal end of the catheter shaft.

11 Claims, 4 Drawing Sheets

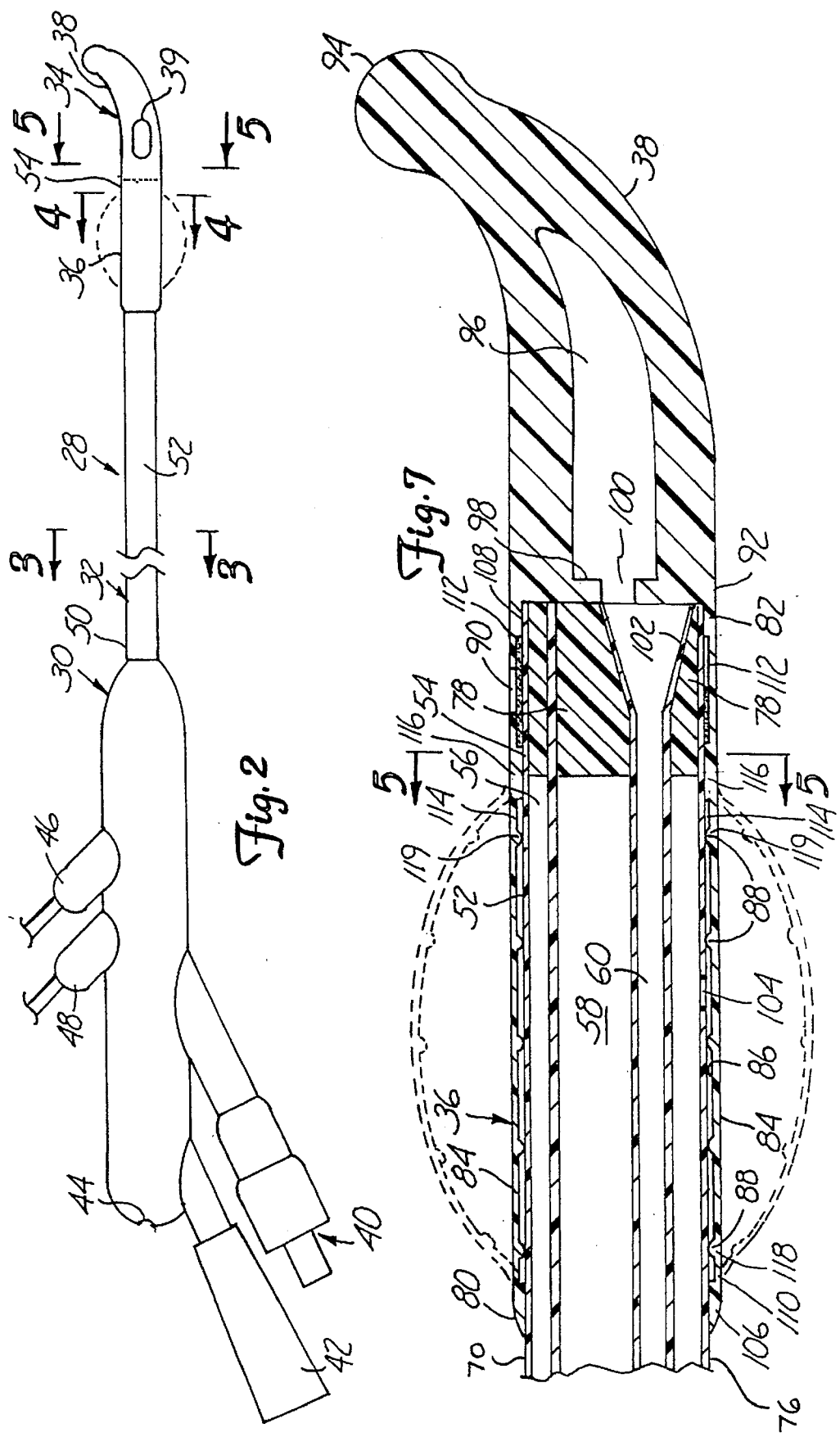

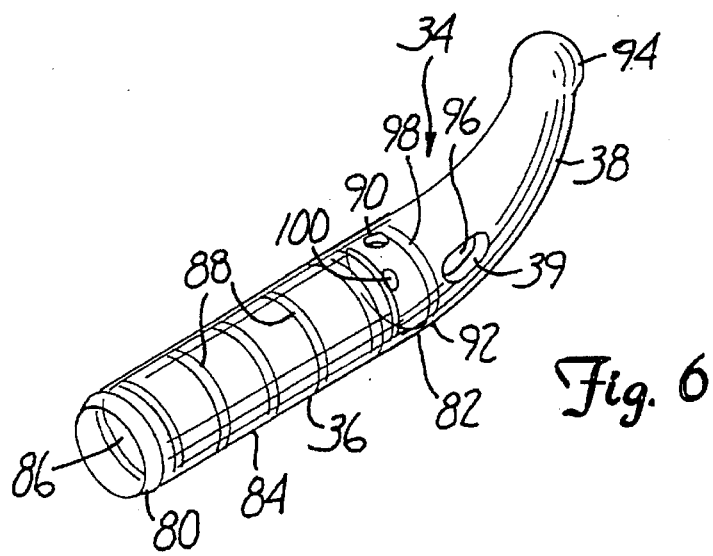
Fig. 6
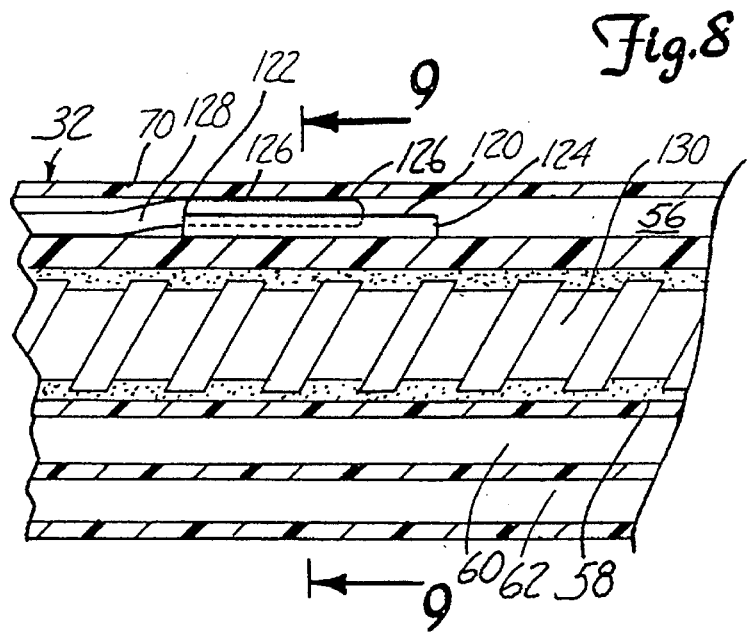
Fig. 8
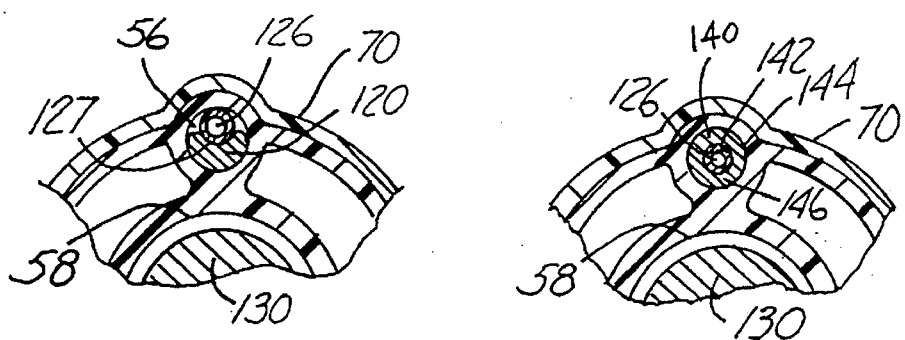
Fig. 9
Fig. 10

UNITARY TIP AND BALLOON FOR TRANSURETHRAL CATHETER

BACKGROUND OF THE INVENTION

The present invention relates to the field of microwave thermal therapy of tissue. In particular, the present invention relates to a catheter for transurethral microwave thermal therapy of benign prostatic hyperplasia (BPH).

The prostate gland is a complex, chestnut-shaped organ which encircles the urethra immediately below the bladder. Nearly one third of the prostate tissue anterior to the urethra consists of fibromuscular tissue that is anatomically and functionally related to the urethra and bladder. The remaining two thirds of the prostate is generally posterior to the urethra and is comprised of glandular tissue.

This relatively small organ, which is the most frequently diseased of all internal organs, is the site of a common affliction among older men: BPH (benign prostatic hyperplasia). BPH is a nonmalignant, bilateral nodular expansion of prostrate tissue in the transition zone, a periurethral region of the prostate between the fibromuscular tissue and the glandular tissue. The degree of nodular expansion within the transition zone tends to be greatest anterior and lateral to the urethra, relative to the posteriormost region of the urethra. Left untreated, BPH causes obstruction of the urethra which usually results in increased urinary frequency, urgency, incontinence, nocturia and slow or interrupted urinary stream. BPH may also result in more severe complications, such as urinary tract infection, acute urinary retention, hydronephrosis and uraemia.

Traditionally, the most frequent treatment for BPH has been surgery (transurethral resection). Surgery, however, is often not an available method of treatment for a variety of reasons. First, due to the advanced age of many patients with BPH, other health problems, such as cardiovascular disease, can warrant against surgical intervention. Second, potential complications associated with transurethral surgery, such as hemorrhage, anesthetic complications, urinary infection, dysuria, incontinence and retrograde ejaculation, can adversely affect a patient's willingness to undergo such a procedure.

A fairly recent alternative treatment method for BPH involves microwave thermal therapy, in which microwave energy is employed to elevate the temperature of tissue surrounding the prostatic urethra above about 45° C., thereby thermally damaging the tumorous tissue. Delivery of microwave energy to tumorous prostatic tissue is generally accomplished by a microwave antenna-containing applicator, which is positioned within a body cavity adjacent the prostate gland. The microwave antenna, when energized, heats adjacent tissue due to molecular excitation and generates a cylindrically symmetrical radiation pattern which encompasses and necroses the tumorous prostatic tissue. The necrosed intraprostatic tissue is subsequently reabsorbed by the body, thereby relieving an individual from the symptoms of BPH.

One method of microwave thermal therapy described in the art includes intrarectal insertion of a microwave antenna-containing applicator. Heat generated by the antenna's electromagnetic field is monitored by a sensor which is positioned near the prostate gland by a urethral catheter. Because of the distance between the rectum and the tumorous prostatic tissue of the transition zone, however, healthy intervening tissue within the cylindrically symmetrical radiation pattern is also damaged in the course of intrarectal treatment. Intrarectal microwave thermal therapy applicators are described in the following references: Eshel et al. U.S. Pat. No. 4,813,429; and A. Yerushahni et al. *Localized Deep Microwave Hyperthermia in the Treatment of Poor Operative Risk Patients with Benign Prostatic Hyperplasia*, 133 JOURNAL OF UROLOGY 873 (1985).

A safer and more effective treatment of BPH is transurethral microwave thermal therapy. This method of treatment minimizes the distance between a microwave antenna-containing applicator and the transition zone of the prostate by positioning a Foley-type catheter-bearing applicator adjacent to the prostate gland within the urethra. Due to the close proximity of the microwave antenna to the prostate, a lesser volume of tissue is exposed to the cylindrically symmetrical radiation pattern generated by the microwave antenna, thereby minimizing the amount of healthy tissue necrosed. Intraurethral applicators of the type described can be found in Turner et al. U.S. Pat. No. 4,967,765 and Hascoet et al. European Patent Application 89403199.6.

Recent improvements in transurethral thermal therapy catheter design have resulted in even more effective application of microwave radiation applied to prostatic tissue. For instance, recent transurethral catheters such as that described in Rudie U.S. Pat. No. 5,413,588, issued May 9, 1995, include shafts having a multiplicity of lumens arranged about a tureen carrying a microwave antenna. The antenna lumen is oriented nearer a first side of the catheter shaft than a second side of the catheter shaft to position the microwave radiation closer to the first side of the catheter. Cooling lumens are arranged about the microwave antenna lumen to absorb a portion of the microwave radiation so that a greater amount of microwave radiation is absorbed on a second side of the catheter shaft than the first side. This arrangement creates an asymmetrical microwave radiation pattern to permit focusing a greater amount of microwave radiation toward a selected tissue, such as prostatic tissue anterior and lateral to the urethra. This transurethral catheter design also includes a lumen to facilitate urinary drainage from the bladder through the urethra during a treatment session.

SUMMARY OF THE INVENTION

The present invention is based upon the recognition that although the catheter disclosed in Rudie et al., U.S. Pat. No. 5,413,588, offers a substantial improvement over previous designs, improvements can still be made to facilitate insertion of the catheter within the urethra while also simplifying manufacture of the catheter.

An intraurethral catheter of the present invention includes a tip mounted on a proximal end of the catheter. The tip comprises a unitary member including an inflatable balloon portion and a tip portion configured to facilitate insertion of the catheter within a urethra. The inflatable balloon portion includes a flexible tubular portion positioned near the proximal end of the shaft wherein the tubular portion envelopes the first and second outer surfaces of the shah and an interior of the tubular portion is in communication with an inflation lumen of the catheter shaft. The wall of the flexible tubular portion selectively expands relative to the outer surface of the catheter shaft upon introduction of an inflation fluid within an interior of the tubular portion. The tubular balloon portion preferably has an inner surface with a plurality of ribs formed thereon to maintain spacing between a side wall of the tubular portion and a side wall of the catheter shaft when the tubular balloon portion is in a nonexpanded state. The tubular balloon portion also has a smooth outer surface that remains relatively flush with an outer surface of the catheter shaft in its nonexpanded state. This gives the catheter tip a low profile facilitating insertion of the tip within the urethra.

A tip portion of the intraurethral catheter tip comprises a flexible curved body having a first end extending from the balloon portion and a second tip end. The tip body includes a tip lumen extending through a length of the body and which is in communication with a urinary drainage lumen of the catheter shaft. A side wall of the flexible curved body can include a side port that communicates with the tip lumen to permit insertion of a guide wire into the tip lumen for facilitating insertion of the intraurethral catheter within a urethra. The side port also permits urine to enter the tip lumen for passage into the urine drainage lumen.

This single piece combined insertion tip and balloon structure permits simple and secure assembly of the tip on a catheter shaft and simplifies manufacture of the tip portion and the balloon. The tip of the present invention permits both an insertion tip and an inflatable retention balloon to be simultaneously secured to an intraurethral catheter shaft in the form of a unitary tip and balloon member. The smooth side wall of the tubular portion defining the expandable balloon provides a low profile for the tip to facilitate insertion of the catheter. The ribs on the interior of the tubular portion defining the balloon maintains spacing between a side wall of the tubular portion and the outer surface of the catheter shaft thereby ensuring expandability of the balloon portion.

BRIEF DESCRIPTION OF THE DRAWINGS

FIG. 2 is a plan view of the urethral catheter of the present invention.

FIG. 6 is a perspective view of a combined tip and balloon of the urethral catheter of the present invention.

FIG. 7 is an enlarged sectional view of the proximal end of the urethral catheter of the present invention.

FIG. 8 is a partial sectional view of the microwave antenna and temperature sensing tureen of the urethral catheter of the present invention.

FIG. 9 is a cross-sectional view of the urethral catheter of FIG. 8 taken along line 9—9.

FIG. 10 is a cross-sectional view of an alternative embodiment of a tubular elongate insert of the present invention.

DETAILED DESCRIPTION OF THE PREFERRED EMBODIMENTS

Figures 1, 11:
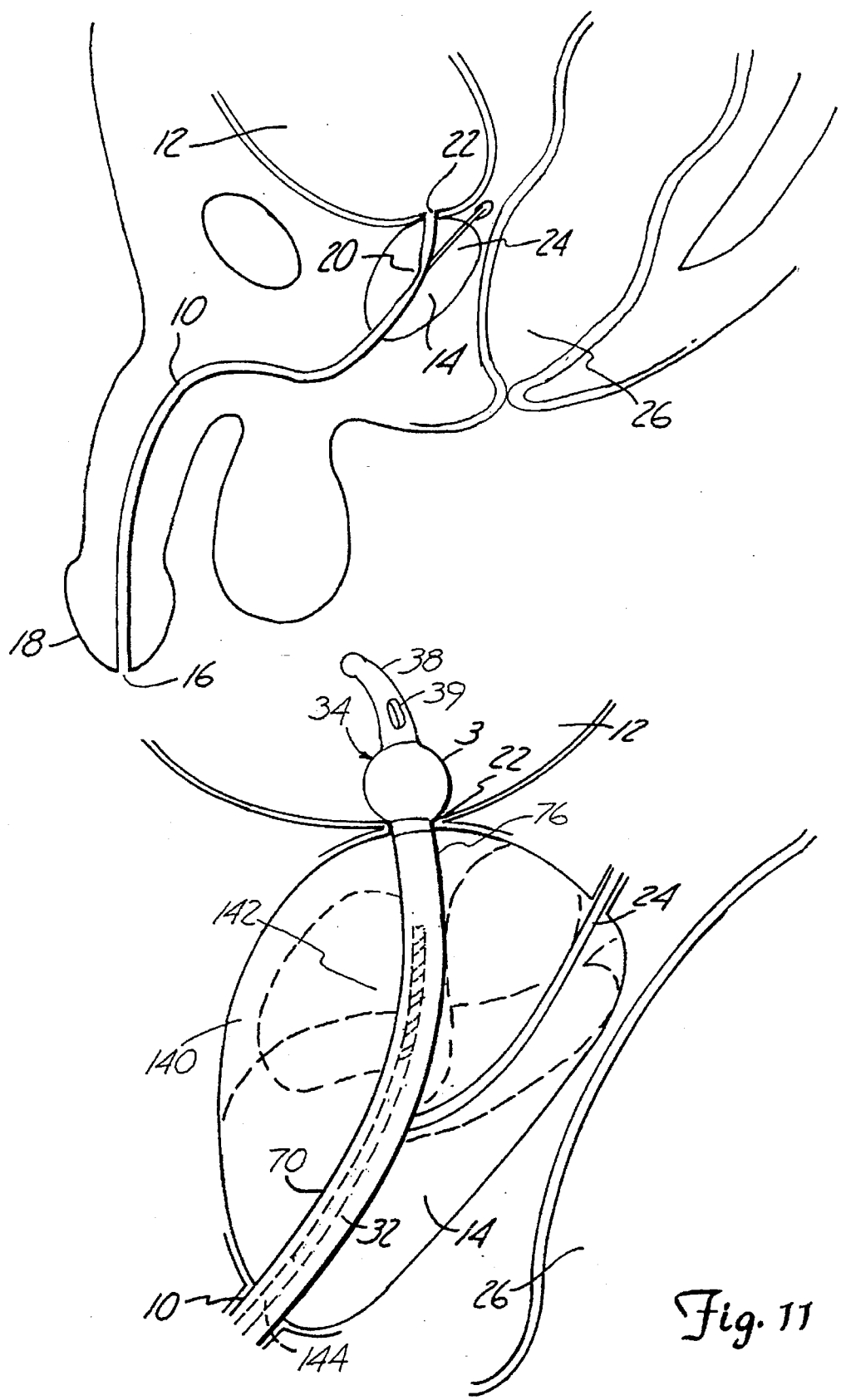
FIG. 1 is a vertical sectional view of a male pelvic region showing the urinary organs affected by benign prostatic hyperplasia.
FIG. 11 is an enlarged view of the male pelvic region of FIG. 1 showing the urethral catheter of the present invention positioned within the prostate region.

FIG. 1 is a vertical sectional view of a male pelvic region showing the effect benign prostatic hyperplasia (BPH) has on the urinary organs. Urethra 10 is a duct leading from bladder 12, through prostate 14 and out orifice 16 of penis end 18. Benign tumorous tissue growth within prostate 14 around urethra 10 causes constriction 20 of urethra 10, which interrupts the flow of urine from bladder 12 to orifice 16. The tumorous tissue of prostate 14 which encroaches urethra 10 and causes constriction 20 can be effectively removed by heating and necrosing the encroaching tumorous tissue. Ideally, with the present invention, only periurethral tumorous tissue of prostate 14 anterior and lateral to urethra 10 is heated and necrosed to avoid unnecessary and undesirous damage to urethra 10 and to adjacent healthy tissues, such as ejaculatory duct 24 and rectum 26. A selective heating of benign tumorous tissue of prostate 14 (transurethral thermal therapy) is made possible by microwave antenna-containing catheter 28 of the present invention, which is shown in FIG. 2.

As shown in FIG. 2, catheter 28 generally includes multi-port manifold 30, multi-lumen shaft 32, and tip 34 which includes balloon portion 36, tip portion 38, and side port 39. Manifold 30 includes inflation port 40, urine drainage port 42, microwave antenna port 44, cooling fluid intake port 46, and cooling fluid exhaust port 48. Ports 40–48 of manifold 30 communicate with corresponding lumens within shaft 32. Manifold 30 is preferably made of medical-grade silicone sold by Dow Corning under the trademark Silastic® Q-7-4850.

Catheter 28 can be employed in a thermal therapy catheter system further including a cooling system, a microwave generating source, and a urethral thermometry unit. These additional elements of a thermal therapy catheter system are disclosed in Rudie et al. U.S. Pat. No. 5,413,588, which is hereby incorporated by reference. In particular, manifold 30 of catheter 28 of the present invention cooperates with a transurethral thermal catheter system in the same manner that manifold 30 disclosed in the Rudie patent cooperates with the multi-lumen catheter, cooling system, microwave generating source, and transurethral thermometry unit disclosed in that patent. For instance, inflation port 40 of manifold 30 of the present invention is adapted for receiving an inflation fluid for inflating balloon portion 36. Urinary drainage port 42 of manifold 30 is adapted to facilitate urine from catheter shaft 32, and antenna port 44 is adapted to receive a microwave antenna for insertion and positioning within the multi-lumen catheter shaft 32. Cooling fluid intake port 46 and cooling fluid exhaust port 48 are cooperable with a cooling system for providing selective flow of cooling fluids within multi-lumen catheter shaft 32.

Shaft 32 is connected to manifold 30 at shaft distal end 50. Shaft 32 is long enough to permit insertion of balloon 36 through urethra 10 and into bladder 12. Shaft 32 is a multi-lumen urethral catheter shaft which is extruded from a flexible, medical-grade silicone sold by Dow Corning under the trademark Silastic® Q-7-4850. The silicone material preferably has a durometer hardness of 80 Shore A.

Figures 3, 4:
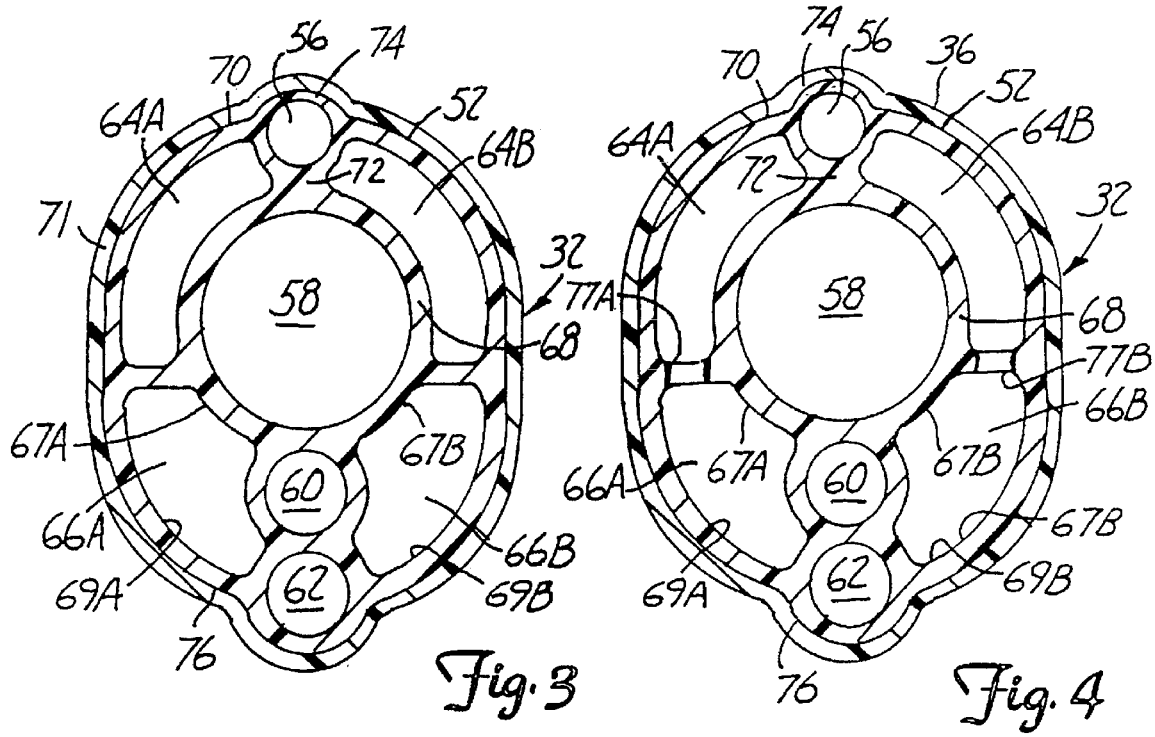
FIG. 3 is a cross-sectional view of the urethral catheter of FIG. 2 taken along line 3—3.
FIG. 4 is a cross-sectional view of the urethral catheter of FIG. 2 taken along line 4—4.

As shown in FIG. 3, multi-lumen shaft 32 includes temperature sensing lumen 56, microwave antenna lumen 58, urine drainage lumen 60, balloon inflation lumen 62, cooling fluid intake lumens 64A and 64B, and cooling exhaust lumens 66A and 66B. Lumens 56–66B generally extend from distal shaft end 50 to proximal shaft end 54. Lumens 56–66B are defined by unitary wall 68 which has a substantially uniform thickness throughout a cross section of catheter shaft 32. Catheter wall 68 preferably has a thickness of 0.009 inches. A center of each of lumens 56–62 is aligned along a longitudinal axis of an elliptical cross section of catheter shaft 32. Protective sheath 71 covers outer surface 52 of catheter shaft 32 and is preferably made of Teflon® to facilitate its advancement within urethra 10.

Temperature sensing lumen 56 is positioned near first side 70 of shaft 32. Temperature sensing lumen 56 has a generally circular cross sectional surface area and is configured to permit insertion of a thermometry sensor within shaft 32 to monitor the temperature of surrounding prostatic tissue when shaft 32 is inserted within urethra 10. Temperature sensing lumen 56 preferably has a diameter of about 0.032 inches.

First modified portion 72 of catheter wall 68 defines a common wall between antenna lumen 58 and temperature sensing lumen 56. First modified wall portion 72 preferably has a thickness (e.g., 0.020 inches) about two times the otherwise substantially uniform thickness of catheter wall 68. Second modified portion 74 of catheter wall 68 defines an outer wall of temperature sensing lumen 56 and preferably has a thickness (e.g., 0.005 inches) about one-half the otherwise substantially uniform wall thickness of catheter wall 68.

Microwave antenna lumen 58 is positioned eccentric to the longitudinal axis of catheter shaft 32, antenna lumen 58 being positioned nearer first side 70 of shaft 32 than second side 76 of shaft 32. Microwave antenna lumen 58 preferably has a generally circular cross-sectional surface area which is larger than a cross-sectional surface area of any of the other respective lumens of catheter shaft 32. Antenna lumen 58 preferably has a diameter of about 0.106 inches. At its distal end, antenna lumen 58 communicates with microwave antenna port 44 of manifold 30. Antenna lumen 58 is adapted for receiving a microwave antenna to be permanently positioned within antenna lumen 58 of shaft 32 near balloon 36 (FIG. 2) so the antenna will be generally situated adjacent benign tumorous tissue of prostate 14 when shaft 32 is properly positioned within urethra 10. A microwave antenna suitable for incorporation into catheter 28 of the present invention is disclosed in Rudie et al. U.S. Pat. No. 5,413,588, issued May 9, 1995, and is hereby incorporated by reference.

Urine drainage lumen 60 is positioned adjacent antenna lumen 58 between antenna lumen 58 and second side 76 of shaft 32. Urine drainage lumen 60 has a generally circular cross-sectional surface area defined by catheter wall 68 and preferably has a diameter of about 0.04 inches. Urine drainage lumen 60 communicates with urine drainage port 42 of manifold 30 at distal shaft end 50 and with tip 34 at proximal shaft end 54 to define a drainage path for urine when tip 34 of catheter 28 is inserted within bladder 12. Urine flows into tip 34 through side port 39 (FIG. 2). Drainage of urine from bladder 12 is necessary due to frequent bladder spasms which occur during transurethral thermal therapy.

Balloon inflation lumen 62 is positioned near second side 76 of shaft 32, generally between urine drainage lumen 60 and second side 76. Balloon inflation lumen 62 preferably has a generally circular cross-sectional surface area defined by catheter wall 68 and preferably has a diameter of about 0.04 inches. Balloon inflation lumen 62 communicates with inflation port 40 of manifold 30 for moving balloon inflation fluid in and out of the balloon inflation lumen 62. Balloon inflation lumen 62 is provided for supplying an inflation fluid to balloon portion 36 of tip 34.

Cooling fluid intake lumens 64A and 64B are positioned circumjacent antenna lumen 58 and first side 70, being located between first side 70 and antenna lumen 58. Cooling fluid intake lumens 64A and 64B are defined by unitary catheter wall 68 and preferably have a generally arc shaped cross-sectional surface area configured to partially surround antenna lumen 58. Cooling lumens 64A and 64B also preferably have a uniform radial thickness. Cooling fluid intake lumens 64A and 64B extend from distal shaft end 50 to proximal shaft end 54. Fluid contained within intake lumens 64A and 64B absorbs a portion of microwave energy emitted by a microwave antenna within antenna lumen 58 to control the volume of prostatic tissue adjacent first side 70 of shaft 32 that is heated above 45° C. Water within intake lumens 64A and 64B also absorbs heat energy generated by microwave energy from adjacent tissues via thermal conduction. Cooling fluid intake lumens 64A, 64B have a radial thickness of about 0.028 inches and have an inner radius of 0.062 inches and an outer radius of 0.09 inches (relative to a focus of the elliptical cross-section of shaft 32 nearest first side 70).

Cooling fluid exhaust lumens 66A and 66B are generally positioned between second side 76 and antenna lumen 58 and have a generally arc-shaped cross-sectional surface area. First portions 67A and 67B of cooling exhaust lumens 66A and 66B are circumjacent antenna lumen 58 and second portions 69A and 69B are circumjacent second side 76 of catheter shaft 32. The generally arc shaped cross-sectional surface area of cooling fluid exhaust lumens 66A and 66B is modified to accommodate the presence of urine drainage lumen 60 between cooling exhaust lumens 66A and 66B. Cooling exhaust lumens 66A and 66B extend from shaft distal end 50 to shaft proximal end 54. Cooling exhaust lumens 66A and 66B are wider in cross section than cooling intake lumens 64A and 64B and have a cross-sectional surface area greater than the cross-sectional surface area of cooling intake lumens 64A and 64B. Cooling fluid exhaust lumens 66A, 66B have an outer radius of 0.09 inches (relative to a focus of the elliptical shaft cross section of shaft 32 nearest second side 76). Portion 67A, 67B of lumens 66A, 66B have an inner radius of 0.062 inches (relative to the focus of the elliptical shaft cross section nearest first side 70).

This greater cross-sectional surface area of exhaust lumens 66A and 66B enable water within exhaust lumen 66A and 66B to be capable of absorbing a greater amount of microwave energy when a microwave antenna disposed within antenna lumen 58 is energized. Given the power output currently used with a microwave antenna such as that disclosed in Rudie et al. U.S. Pat. No. 5,413,588, the temperature of tissue adjacent second side 76 of shaft 32 will remain below about 45° C. This prevents the portion of urethra 10 adjacent second side 76 from being overheated and damaged when a microwave antenna within antenna lumen 58 is energized.

Cooling intake lumens 64A and 64B and exhaust lumens 66A and 66B cooperate with a cooling system via ports 46 and 48 of manifold 30 to provide a selectively controlled flow of fluid through cooling lumens 64A, 64B, 66A, and 66B during a treatment session. This arrangement achieves a desired cooling radiant surrounding a microwave antenna energized within antenna lumen 58 while catheter shaft 32 is within a urethra 10. Cooling intake lumens 64A, 64B and cooling exhaust lumens 66A, 66B can be used with a cooling system under the treatment parameters as described in Rudie et al. U.S. Pat. No. 5,413,588, (earlier incorporated by reference) and under the treatment parameters disclosed in pending application U.S. Ser. No. 08/309,137, filed Sep. 20, 1994.

Cooling fluid intake lumens 64A and 64B are in communication with cooling exhaust lumens 66A and 66B, respectively, near proximal shaft end 54 of catheter shaft 32 adjacent balloon portion 36 (FIG. 2). As shown in FIG. 4, a portion of catheter wall 68 defining a common wall between cooling intake lumen 64A and cooling exhaust lumen 66A has been removed creating hole 77A to permit communication between the respective lumens. Similarly, a portion of catheter wall 68 defining a common wall between cooling intake lumen 64B and cooling exhaust lumen 66B has been removed creating hole 77B to allow communication between the respective lumens 64B and 66B. This configuration permits cooling fluid that is flowing proximally through cooling intake lumens 64A and 64B to enter cooling exhaust lumens 66A and 66B, respectively, to establish a cooling fluid flow loop that cooperates with a cooling system connected to manifold 30.

Figure 5:
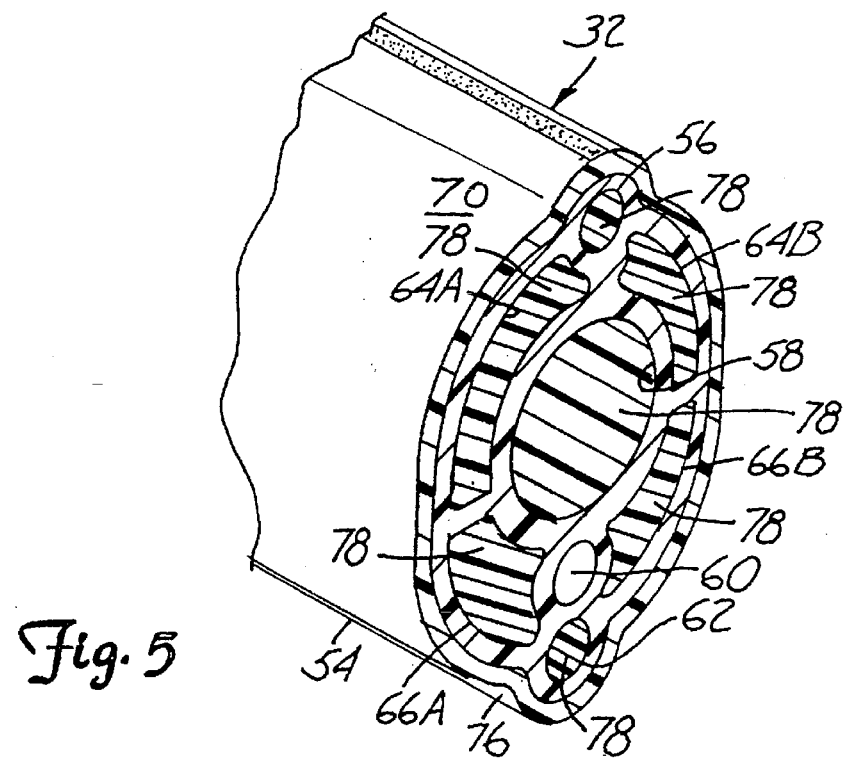
FIG. 5 is a perspective view of a proximal portion of the urethral catheter with the proximal end portion taken in section from line 5—5 of FIG. 2.

FIG. 5 illustrates a cross section of catheter shaft 32 adjacent a shaft end 54 just proximal to balloon 36 (see FIG. 2). At this location, temperature sensing lumen 56, antenna lumen 58, inflation lumen 62, cooling intake lumens 64A and 64B, and cooling exhaust lumens 66A and 66B, are closed by silicone plug material 78 sealing each of these lumens at proximal shaft end 54. However, urine drainage lumen 60 remains open at proximal shaft end 54 so that urine from the bladder may pass through tip 34 and into urine drainage lumen 60.

As shown in FIG. 6, tip 34 comprises a unitary member including balloon portion 36 and tip portion 38. Balloon portion 36 is a flexible tubular portion having distal end 80, proximal end 82, side wall 84, inner surface 86, ribs 88, and hole 90. Side wall 84 of tubular balloon portion 36 extends between distal end 80 and proximal end 82 and has inner surface 86 with ribs 88 formed thereon extending circumferentially on the inner surface 86. Ribs 88 are visible in FIG. 6 since flexible tubular portion of balloon portion 36 is preferably made from a translucent material. Side wall 84 of tubular balloon portion 36 includes hole 90 formed adjacent proximal end 82.

Tip portion 38 comprises a flexible curved body having distal end 92, proximal tip end 94, tip lumen 96, dividing wall 98, and hole 100. Tip lumen 96 extends through a portion of the tip body and communicates with side port 39. Side port 39 permits insertion of a guide wire (not shown) into tip lumen 96 to facilitate insertion of intraurethral catheter 28 within urethra 10 in a manner well known in the art. Dividing wall 98 at distal end 92 defines a border between balloon portion 36 and tip portion 38. Wall 98 also defines a distal end of tip lumen 96 and has hole 100 formed therein to permit communication between tip lumen 96 and an interior of tubular balloon portion 36.

Tip 34 is formed by liquid injection molding from a flexible, medical-grade silicone sold by Dow Corning under the trademark Silastic® Q-7-4850. The silicone preferably has a material hardness of 20 Shore A, which is relatively soft to provide an atraumatic tip. Tip 34 can also include a radiopaque filler such as barium sulfate added to the silicone material to make tip 34 observable under fluoroscopy.

Tip 34 preferably has a length of 1.95 inches including tip portion 38 which preferably has a length of 0.84 inches. Tubular portion 36 preferably has a length of 1.11 inches including the ribbed portion which has a length of 0.64 inches. Side wall 94 preferably has a thickness of 0.01 inches while ribs 88 preferably have a radius of 0.01 inches and are spaced longitudinally with respect to each other by 0.16 inches. Tubular portion 36 has an elliptical cross section and has a radius of about 0.110 inches, wherein the foci of the ellipse are separated by 0.053 inches. Side wall 94 of tubular portion is capable of elongating up to 400% so that an elliptical cross section of balloon portion 36 when expanded has a cross sectional area about 4 times its cross sectional area in a nonexpanded state.

FIG. 7 provides a more detailed view of catheter shaft 32 and tip 34 at proximal shaft end 54. Proximal shaft end 54 of catheter 28 fits snugly within tubular balloon portion 36 of tip 34 with utmost proximal shaft end 54 resting against dividing wall 98 of tip 34 and outer surface 52 of catheter shaft 32 in contact with multiple structures defining an interior of tubular balloon portion 36.

As shown in FIG. 7, urine drainage lumen 60 further includes expanded diameter portion 102 while inflation lumen 62 further includes hole 104. Temperature sensing lumen 56, antenna lumen 58, and inflation lumen 62 further include silicone plug material 78 filled within their proximal ends. Balloon portion 36 of tip 34 further includes first collar 106, second collar 108, first well 110, second well 112, third well 114, adhesive dam 116, first rib 118, and second rib 119.

Expanded diameter section 102 of urine drainage lumen 60 has a generally conical shape and communicates with tip lumen 96 via hole 100 in wall 98 to permit urine flow therethrough. Hole 104 of inflation lumen 62 permits communication between inflation lumen 62 and an interior of balloon portion 36 for inflating and deflating balloon portion 36.

Expanded diameter portion 102 of urine drainage lumen 60 is formed at the time silicone plug material 78 is introduced into the other lumens of shaft 32 at proximal shaft end 54. In particular, a syringe tip is introduced into urine drainage lumen 60 at proximal shaft end 54 and maintained in that position while silicone plug material 78 is introduced into all of the remaining lumens defining catheter shaft 32. The introduction of silicone plug material 78 includes the application of heat to proximal shaft end 54, thereby causing urinary drainage lumen 60 to permanently expand and reform about the shape of the syringe tip. Upon setting of the silicone plug material 78, the syringe tip is removed from proximal shaft end 54 resulting in urine drainage lumen 60 having expanded diameter portion 102 and each of the other respective lumens of catheter shaft 32 having sealed ends filled with silicone plug material 78.

First collar 106 of balloon portion 36 defines distal end 80 while second collar 108 defines proximal end 82 with side wall 84 extending therebetween. First well 110 defines a reservoir formed between first collar 106, first rib 118, and side wall 84 while second well 112 defines a reservoir formed between second collar 108, side wall 84, and adhesive dam 116. Third well 114 defines a reservoir formed between adhesive dam 116, side wall 84, and second rib 119.

To secure tip 34 onto proximal shaft end 54, tubular portion 36 is slip fit over proximal shaft end 54 into the position shown in FIG. 7. Next, tubular portion 36 is secured about proximal shaft end 54 with an adhesive. Adhesive is introduced between first collar 106 and shaft outer surface 52 of shaft 32 to create a sealed connection therebetween. First well 110 catches any excess adhesive that wicks proximally beyond first collar 106.

Side hole 90 is used to introduce adhesive between second collar 108 and shaft outer surface 32 at utmost shaft proximal end 54. Second well 112 receives adhesive introduced through side hole 90 while adhesive dam 116 blocks adhesive from migrating distally toward inner surface 86 of side wall 84. Third well 118 acts as an additional reservoir for catching excess adhesive migrating past adhesive dam 116.

With first collar 106 and second collar 108 of tubular portion 36 sealingly connected about shaft outer surface 52, side wall 84 remains free to expand relative to shalt outer surface 52 upon introduction of inflation fluid within an interior of balloon portion 36 (via inflation lumen 62 through hole 104). Ribs 88 remain spaced slightly from outer surface 52 and maintain spacing between inner surface 86 of side wall 84 and outer surface 52 of catheter shaft 32. This prevents the silicone material forming balloon portion 36 from sticking to the silicone material forming shaft outer surface 52. In the absence of ribs 88, inner surface 86 of side wall 84 would tend to stick to shaft outer surface 52 and thereby inhibit inflation and expansion of side wall 84.

Tubular portion 36 is positioned on proximal shaft end 54 so that side wall 84 can be expanded within bladder 12 to maintain a proximal end of a microwave antenna (within catheter shaft 32) spaced at least 4 millimeters proximally from the opening of the bladder 12. This positions the microwave antenna within urethra 10 so that healthy prostatic tissue between a tip of the microwave antenna and bladder 12 is preserved.

As shown in FIG. 8, an alternative embodiment of catheter shaft 32 further includes elongate insert 120. Elongate insert 120 includes first end 122 and second end 124. Elongate insert 120 is positioned within temperature sensing lumen 56 alongside sensor 126 of thermal sensing device 128 adjacent microwave antenna 130 positioned within antenna lumen 58. Elongate insert 120 displaces sensor 126 of thermal sensing device 128 radially away from antenna 130 and toward first side 70 of catheter shaft 32.

FIG. 9 illustrates a cross-sectional view of elongate insert 120. Elongate insert 120 has a generally crescent shaped cross-sectional surface area including a concave surface and has a width approximately one-half the diameter of temperature sensing lumen 56. Concave surface 127 of elongate insert 120 is positioned circumjacent sensor 126 between thermal sensing device 128 and antenna lumen 58 to move sensor 126 within temperature sensing lumen 56 as far away as possible from microwave antenna 130 and cooling lumens 64A and 64B. This arrangement increases the accuracy of temperature measurements of surrounding prostatic tissue adjacent shaft first side 70 by better insulating sensor 126 from both heating (microwave antenna) and cooling (cooling fluid) sources within catheter shaft 32. Elongate insert 120, in filling up a portion of the cross sectional area within temperature sensing lumen 56, effectively eliminates excess spacing within lumen 56 that is necessary to permit insertion of thermal sensing device 128 within lumen 56.

Elongate insert 120 can be inserted into temperature sensing lumen 56 either before or after thermal sensing device 128 is positioned within temperature sensing lumen 56. Elongate insert 120 is introduced into temperature sensing lumen 56 by making a cut in first side 70 of catheter shaft 32 adjacent temperature sensing lumen 56 and advancing elongate insert 120 distally through temperature sensing lumen 56 until elongate insert 120 is completely within temperature sensing 56 and resting on an inner wall of temperature sensing lumen 56. Elongate insert 120 is then held in place against the inner wall of temperature sensing lumen 56 until sensor 126 is properly positioned relative to elongate insert 120. Thereafter, the slit made in first side 70 of catheter shaft 32 is sealed using an adhesive filler. Elongate insert 120 has a length of about one to two inches, a thickness at its center of about 0.013 inches, and a width between its outer edges of about 0.32 inches. Elongate insert 120 is preferably formed from a Teflon material to facilitate sliding movement of sensor 126 relative to insert 120.

As shown in FIG. 10, tubular elongate insert 140 provides an alternative embodiment to crescent shaped elongate insert 120. Tubular elongate insert 140 includes inner surface 142, outer surface 144 and wall 146 defined therebetween. Tubular insert 140 is positioned within temperature sensing lumen 56 and surrounds sensor 126 of thermal sensing device 128. Like elongate insert 120, tubular insert 140 displaces sensor 126 away from antenna 130 and cooling lumens 64A and 64B toward first side 70 of catheter shaft 32, thereby eliminating excess space within temperature sensing lumen 56 and increasing the accuracy of temperature measurements of the surrounding prostatic tissue.

Tubular insert 140 is placed within temperature sensing lumen 58 according to the insertion method described for elongate insert 120. Tubular insert 140 is preferably formed from a Teflon® material to facilitate sliding movement of sensor 126 relative to tubular insert 140. Tubular insert 140 has a length of about one to two inches, wall 146 has a uniform radial thickness of about 0.007 inches, and outer surface 144 has a diameter of about 0.032 inches.

In use, catheter 28 of the present invention including multi-lumen catheter shaft 32 and tip 34 including balloon portion 36 is employed according to the insertion method and treatment method described in Rudie et al. U.S. Pat. No. 5,413,588. Additional urethral treatment parameters can be employed with catheter 28 of the present invention such as that described in U.S. Pat. application Ser. No. 08/309,137 filed Sep. 20, 1994 and hereby incorporated by reference.

FIG. 11 shows an enlarged view of the male pelvic region of FIG. 1 with catheter 28 properly positioned within urethra 10. Shaft 32 is positioned within urethra 10 with second side 76 of shaft 32 oriented toward rectum 26. Cooling fluid exhaust lumens 66A, 66B are oriented posteriorly, toward rectum 26 and cooling fluid intake lumens 64A, 64B are oriented anteriorly toward fibromuscular tissue 140 of prostate 14. The portion of transition zone 142 anterior and lateral to urethra 10 is the most frequent location of the tumorous tissue growth which causes BPH. Since cooling fluid exhaust lumens 66A, 66B are capable of absorbing more microwave energy than cooling fluid intake lumens 64A, 64B, the radiation patterns created by microwave energy emitted from antenna 144 are asymmetrical. Thus, a relatively large volume of tissue enveloping the anterior portion of transition zone 142, adjacent first side 70, is heated to a temperature above about 45° C., which effectively necroses the tumorous tissue of prostate 14 which encroaches upon urethra 10. In comparison, the temperature of tissue adjacent second side 76 remains below about 45° C., thereby eliminating the harmful effects of the microwave energy to ejaculatory duct 24 and rectum 26.

Catheter 28 of the present invention including multi lumen shaft 32 and tip 34 yield numerous advantages over the prior art. First, multi lumen catheter shaft 32 is configured to maximize exposure of its cooling lumens to an antenna lumen carrying a microwave antenna. This optimized configuration is established by having cooling fluid intake and exhaust lumens with a generally arc shaped cross-sectional area which substantially surround an antenna lumen having a generally circular cross-sectional area. These lumens are defined by a single unitary wall having a substantially uniform wall thickness arranged to maximize the cross-sectional surface area of the cooling lumens relative to the antenna lumen. Second, a urine drainage lumen of the present invention has a generally circular cross-sectional surface area which tends to remain open even when an intraurethral catheter of the present invention is disposed within a portion of a urethra which bends the intraurethral catheter. In addition, the generally circular cross-sectional area of the urine drainage lumen disposed adjacent the antenna lumen minimizes the relative surface area and exposure between the urine drainage lumen and the antenna lumen. This reduces the effect that variable urine flow within the urine drainage lumen has on microwave antenna tuning.

Finally, the lumens of multi lumen catheter shaft 32 are arranged and shaped to increase the structural integrity of catheter shaft 32 while maximizing the surface area of each of the respective lumens. This is accomplished by defining the respective lumens by a single unitary wall having a substantially uniform wall thickness and by selecting optimal shapes of the cross-sectional surface area of the lumens.

A tip of catheter of the present invention also has numerous advantages. First, a tip comprising a single unitary member including an insertion tip and an inflatable balloon portion greatly simplifies assembly of the catheter. The tip can simply be slip fit over a proximal end of the catheter shaft and secured thereto with an adhesive. The insertion tip portion facilitates insertion and guidance of the catheter of the present invention within the urethra. A balloon of a tip of the present invention is constructed to maintain a low profile in its deflated state to facilitate insertion and passage of the catheter within a urethra. Unlike prior art balloon designs, a balloon of a tip of the present invention does not have any excess material or winged portions which must be folded down or compressed during insertion of or passage of the balloon through the urethra. Rather, the unique structure of a balloon of the tip of the present invention yields a balloon which remains relatively flat in its deflated state during passage through the urethra. A tubular portion comprising a balloon of the present invention is arranged and configured to facilitate introducing adhesive for sealing the balloon about an outer surface of the catheter shaft without compromising an effective length of the inflatable portion of the balloon caused by wicking of the adhesive toward an anterior portion of the balloon.

Although the present invention has been described with reference to preferred embodiments, workers skilled in the art will recognize that changes may be made in form and detail without departing from the spirit and scope of the invention.

What is claimed is:

1. An intraurethral catheter comprising:
an elongate, generally tubular shaft having a first end, a second end, and an outer surface and at least one lumen extending between the first end and the second end of the shaft; and
a tip mounted on the second end of the shaft, the tip comprising a monolithic member including an inflatable balloon portion and a tip portion extending from the balloon portion and configured to facilitate insertion of the catheter within a urethra, the balloon portion being arranged and configured to slip fit over and be secured on the shaft second end, thereby securing the tip portion to the shaft.

2. The catheter of claim 1 wherein the inflatable balloon portion is a flexible tubular portion having a first end and a second end and is positioned near the second end of the shaft wherein the tubular portion envelopes the outer surface of the shaft and the first and second ends of the tubular portion are sealingly connected to the outer surface of the shaft the flexible tubular portion having a wall that is expandable relative to the outer surface of the catheter shaft, wherein the outer surface of the catheter shaft and the expandable wall define a space therebetween that is in communication within at least one of the lumens of the catheter shaft.

3. The catheter of claim 2 wherein the tubular balloon portion includes a side wall having an inner surface with a plurality of ribs formed thereon extending circumferentially on the inner surface.

4. The catheter of claim 2 wherein the tubular portion includes a sidewall having a hole formed therein to facilitate securing the balloon portion of the tip to the catheter shaft.

5. The catheter of claim 1 wherein the tip portion comprises a flexible curved body having a first end extending from the balloon portion and a second tip end, the curved tip body including a tip lumen extending through a length of the curved tip body and being in communication with at least one lumen of the catheter shaft.

6. The catheter of claim 5 wherein the tip portion further includes a side wall having a side port in communication with the tip lumen permitting insertion of a guide wire into the tip lumen to facilitate insertion of the intraurethral catheter within a urethra.

7. The catheter of claim 6 wherein the first end of the curved tip body defines a dividing wall between the balloon portion and the tip portion, the wall defining an end of the tip lumen and having a hole formed therein to permit communication between the tip lumen and one of the lumens of the catheter shaft.

8. An intraurethral catheter comprising:
an elongate shaft having a first end, a second end, an outer surface, and at least one lumen which extends between the first end and the second end of the shaft; and
a tip formed of a monolithic member secured to the second end of the shaft, the tip including a balloon portion and a tip portion extending from the balloon portion for guiding the catheter within a urethra, the balloon portion being configured and arranged to slip fit over and be secured on the shaft second end and having a first end and a second end with a distensible wall extending therebetween defining an inflatable balloon, the balloon enveloping the outer surface of the shaft and the first and second ends of the balloon portion being sealingly connected to the outer surface of the shaft wherein the outer surface of the shaft and the distensible wall define a space therebetween that is in communication at least one of the lumens of the shaft to permit inflation of the balloon portion.

9. An intraurethral catheter comprising:
an elongate, generally tubular shaft having a first end, a second end, and an outer surface and at least one lumen extending between the first end and the second end of the shaft; and
a tip mounted on the second end of the shaft, the tip comprising an inflatable flexible tubular balloon portion and a tip portion configured to facilitate insertion of the catheter within a urethra, the balloon portion having a first end and a second end and a side wall having an inner surface with a plurality of ribs formed thereon extending circumferentially on the inner surface, the tubular balloon portion enveloping the outer surface of the shaft with the first and second ends of the tubular balloon portion being sealingly connected to the outer surface of the shaft; wherein the side wall of the tubular balloon portion is expandable relative to the outer surface of the catheter shaft, the outer surface of the catheter shaft and the expandable wall defining a space therebetween that is in communication within at least one of the lumens of the catheter shaft.

10. An intraurethral catheter comprising:
an elongate, generally tubular shaft having a first end, a second end, and an outer surface and at least one lumen extending between the first end and the second end of the shaft; and
a tip mounted on the second end of the shaft, the tip comprising an inflatable flexible tubular balloon portion and a tip portion configured to facilitate insertion of the catheter within a urethra, the balloon portion having a first end, a second end, and a side wall, the first and second ends of the tubular balloon portion being sealingly connected to the outer surface of the shaft so that the tubular balloon portion envelopes the outer surface of the shaft and where the side wall of the tubular balloon portion is capable of expanding relative to the outer surface of the catheter shaft, the outer surface of the catheter shaft and the expandable wall defining a space therebetween that is in communication within at least one of the lumens of the catheter shaft; and means for maintaining a side wall of the tubular balloon portion at at least a predetermined distance of separation from the outer surface of the catheter shaft, the maintaining means located on the side wall.

11. An intraurethral catheter comprising:

an elongate, generally tubular shaft having a first end, a second end, and an outer surface and at least one lumen extending between the first end and the second end of the shaft; and a tip mounted on the second end of the shaft, the tip comprising an inflatable flexible tubular balloon portion and a tip portion configured to facilitate insertion of the catheter within a urethra, the tubular balloon portion being sealingly connected about the outer surface of the catheter shaft and having an expandable wall portion with an inner surface having at least one rib defined thereon, the expandable wall portion and the outer surface of the catheter defining a space that is in communication with at least one of the lumens of the shaft.

* * * * *

UNITED STATES PATENT AND TRADEMARK OFFICE
CERTIFICATE OF CORRECTION

PATENT NO. : 5,645,528
DATED : JULY 8, 1997
INVENTOR(S) : SCOTT P. THOME

It is certified that error appears in the above-indentified patent and that said Letters Patent is hereby corrected as shown below:

Col. 2, line 2, delete "Yerushahni", insert --Yerushalmi--

Col. 2, line 25, delete "tureen", insert --lumen--

Col. 2, line 55, delete "shah", insert --shaft--

Col. 3, line 49, delete "tureen", insert --lumen--

Col. 7, line 64, delete "94", insert --84--

Col. 8, line 65, delete "shalt", insert --shaft--

Col. 12, line 5, before "body", insert --tip--

Signed and Sealed this

Sixteenth Day of December, 1997

BRUCE LEHMAN

*Attest:*

*Attesting Officer*   Commissioner of Patents and Trademarks